(12) United States Patent
Etienne (10) Patent No.: US 11,330,847 B2
(45) Date of Patent: May 17, 2022

(54) GARMENT COMPRISING AN ABSORBENT CROTCH PANEL SYSTEM

(71) Applicant: Crystal Bobby Etienne, Massapequa Park, NY (US)

(72) Inventor: Crystal Bobby Etienne, Massapequa Park, NY (US)

(73) Assignee: Crystal Bobby Etienne, Massapequa Park, NY (US)

( * ) Notice: Subject to any disclaimer, the term of this patent is extended or adjusted under 35 U.S.C. 154(b) by 107 days.

(21) Appl. No.: 16/570,395

(22) Filed: Sep. 13, 2019

(65) Prior Publication Data

US 2020/0000155 A1 Jan. 2, 2020

Related U.S. Application Data

(63) Continuation-in-part of application No. 14/864,100, filed on Sep. 24, 2015, now abandoned.

(51) Int. Cl.
*A41B 9/12* (2006.01)
*A41B 9/00* (2006.01)
*A41D 7/00* (2006.01)

(52) U.S. Cl.
CPC ............ *A41B 9/12* (2013.01); *A41B 9/004* (2013.01); *A41D 7/005* (2013.01); *A41B 2300/20* (2013.01)

(58) Field of Classification Search
CPC ........... A41B 9/004; A41B 9/005; A41B 9/04; A41B 9/12; A41B 2300/20

USPC ............................................................. 2/406
See application file for complete search history.

(56) References Cited

U.S. PATENT DOCUMENTS

| | | | | |
|---|---|---|---|---|
| 5,558,659 A | * | 9/1996 | Sherrod | A61F 13/471 604/385.26 |
| 7,651,487 B2 | * | 1/2010 | Niki | A61F 13/471 604/385.101 |
| 9,198,807 B2 | * | 12/2015 | Evenson | A61F 13/72 |
| 10,441,479 B2 | | 10/2019 | Griffiths | |
| 10,441,480 B2 | | 10/2019 | Griffiths | |
| 2012/0010582 A1 | * | 1/2012 | Newnam | A61F 13/505 604/360 |
| 2014/0013490 A1 | * | 1/2014 | Evenson | A61F 13/496 2/400 |

* cited by examiner

*Primary Examiner* — Timothy K Trieu
(74) *Attorney, Agent, or Firm* — K&L Gates LLP (57) ABSTRACT

A crotch panel system is disclosed. The crotch panel system comprises a bottom crotch panel, a unitary top layer crotch panel defining a shaped hole in the center, and an additional crotch panel layer attached to the bottom crotch panel. The shaped hole defined in the unitary top layer crotch panel defines a perimeter. An elastic border extends around the perimeter of the shaped hole, and the elastic border is configured to stretch to facilitate insertion of an object. The additional crotch panel layer is attached to the bottom crotch panel to provide stability of the object placed within the crotch panel system.

20 Claims, 8 Drawing Sheets

GARMENT COMPRISING AN ABSORBENT CROTCH PANEL SYSTEM

CROSS-REFERENCE TO RELATED APPLICATIONS

This application is a continuation-in-part application claiming priority under 35 U.S.C. § 120 to U.S. patent application Ser. No. 14/864,100, filed on Sep. 24, 2015, entitled UNDERGARMENT WITH A CROTCH AREA TOP PANEL LAYER OVER AND ADJACENT TO A BOTTOM PANEL LAYER TO SECURE AND CONCEAL OBJECTS IN PLACE, the entire disclosure of which is hereby incorporated by reference herein.

BACKGROUND

Undergarments with a crotch area are used by females in the categories of panties, underwear, briefs, and hosiery. Every time a female has her menstrual cycle or period, she has the need of a removable object, such as a sanitary pad, paper towel, sanitary towel, panty liner or absorbent pad to stay in place in the crotch area, and be concealed in the garment. A female wants to be comfortable and worry free, and not have to worry about the removable object slipping off, falling out of her undergarment, or out of her crotch area on the sides, or easing upwards or out, a female also wants a solution to prevent embarrassment or awkwardness of the object being visible to the human eye. Therefore, a need exists for an undergarment with a crotch area to help conceal objects placed in the crotch area, and a solution that will allow objects placed in the crotch area of undergarments to be able to be securely in place to prevent slipping, movement, or falling out of the object from the undergarment in the crotch area. All females that experience menstruation or periods will benefit from the invention. The invention eliminates the female from having to worry about the object falling out of the crotch area, shifting, and being seen from the front or back of the undergarment by the human eye.

Additional aspects, and any features, along with any combination of advantages of the invention will be apparent from this specification and detailed description of the invention. It is also understood the following descriptions will describe the embodiment, framework, and features of the invention consistently to understand the claims. Drawings are incorporated and included into this specification to provide a clear understanding of the claimed subject matter.

SUMMARY

The present invention relates generally to the field of undergarments with a crotch area in the category of panties, briefs, underwear, bodysuits, stockings, and hosiery, having a top layer fabric panel in the crotch area, in which the top crotch panel fabric is adjacent to the bottom crotch panel, and cut in the center to form a shape of a octagon, square, oval, round, triangle, rectangle, or circular shape and attached to the bottom crotch area, acting as an enclosure to secure objects in place in the crotch area, by the center edges of the perimeter, with elastic around the shape, keeping the object secure and concealed from the outside of the garment to be unseen by the human eye. Particular removable objects are a sanitary pad, panty liner, paper towel, sanitary napkin, sanitary towel, and absorbent pad in the crotch area.

The present invention features undergarments with a top crotch area panel over, attached, and adjacent to the bottom crotch area of the undergarment, and cut into a shape in the middle, the cut out shape is outlined in elastic around the perimeter of the top layer crotch area to securely hold objects in place and be concealed from the human eye from the outside of the undergarment. The undergarments, in the crotch area has a bottom crotch panel, and a top crotch panel attached to the bottom crotch panel, which is also adjacent to the bottom crotch panel, the top layer panel has a hole in the center in the shape of either a rectangle, round, circular, octagon, oval, triangle, or square, and the top layer crotch panel has an elastic perimeter around the hole, which holds the objects in its place. The undergarments top and bottom layer panel are attached and sewed to the right and left leg openings of the undergarment, and the front panel and back panel of the undergarment are seamless so that you cannot see the object visible of the human eye.

FIGURES

The various aspects described herein, both as to organization and methods of operation, together with further objects and advantages thereof, may best be understood by reference to the following description, taken in conjunction with the accompanying drawings as follows.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Before explaining various aspects of garments and absorbent crotch panel systems in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Below is a list of the elements which correspond to the element referred to:

100 the undergarment with a top crotch area panel with a shaped hole in the center, whereas the shaped hole is finished by elastic around the perimeter of the center hole, and attached and adjacent to the bottom crotch area panel to secure and conceal objects in between the top crotch area panel and bottom crotch area panel;

105 bottom crotch panel;
110 elastic perimeter of top crotch panel hole;
111 center shaped hole;
115 front panel;
120 back panel;
125 top crotch panel with center shaped hole;
130 object placed between the top and bottom crotch panel;
135 left leg opening;
140 right leg opening;
145 front view of undergarment with crotch area;
150 back view of undergarment with crotch area; and
155 elastic waistband.

The present invention will now be described in detail in reference to the accompanied drawings. The drawings consist of exemplary parts put together which create the invention. However the invention may be embodied in many different shapes and forms and should not be limited just to the represented embodiment herein. The exemplary parts are provided herein to convey the invention in terms that one with normal, or any person with ordinary art skills will understand how to create, and use the invention.

In reference to FIGS. 1A-5, the present invention features a undergarment system (100) that includes a front panel (115) and a back panel (120), and a top crotch panel with a center shaped hole (125) and elastic perimeter of top crotch panel hole (110) attached, joined, and adjacent to the bottom crotch panel (105). The undergarment have the styles of panties, thongs, boy shorts, underwear, briefs, high-cut, bikini, hipster, tanga, hosiery, stockings, cheeky panty, and bodysuit. The top crotch panel with center shaped hole (125) have the shape of a rectangle, circular, round, square, octagon, triangle, or oval. (0026) A left leg opening (135) and a right leg opening (140) are attached to the top crotch panel with center shaped hole (125) bottom crotch panel (105) front panel (115) and back panel (120). The elastic waistband (155) joins the front panel (115) and back panel (120). The front panel (115) back panel (120) bottom crotch panel (105) top crotch panel with center shaped hole (125) are all made with materials such as cotton, lycra, nylon, lace, polyester, or spandex fabrics and are all sewn together.

In some embodiments, the undergarments can have more than 2 crotch area panels. The purpose of the multiple crotch area panels is to provide assistance and more stability of the object placed between the (120) bottom crotch panel (105) top crotch panel with center shaped hole (125) and elastic perimeter of top crotch panel hole (110).

Various modifications of the invention, in addition to those described herein, will be obvious to those skilled in the art of the descriptions herein. All modifications are intended to fall within the scope of the claims. Though, it has been shown and described as the preferred embodiment of the invention, it will be apparent and obvious to those skilled in the art that modifications may be made thereto which do not exceed the scope of the claims. Therefore, the scope of the invention is only to be limited by the claims herein.

A garment is disclosed, wherein the garment comprises a discrete fluid collecting system. The fluid collecting system is angled to collect fluid flow, such as fluid from a menstruation cycle and/or fluid from incontinence, for example. The garment is designed to provide security, comfort, and/or leak-free peace of mind for a user. The garment is designed to prevent leaks and/or odors while being devoid of plastics and/or polyurethane laminate (PUL). The garment is envisioned as an undergarment, a swimsuit, active wear, and/or any other suitable type of garment. The garment is reusable.

Figure 1A:
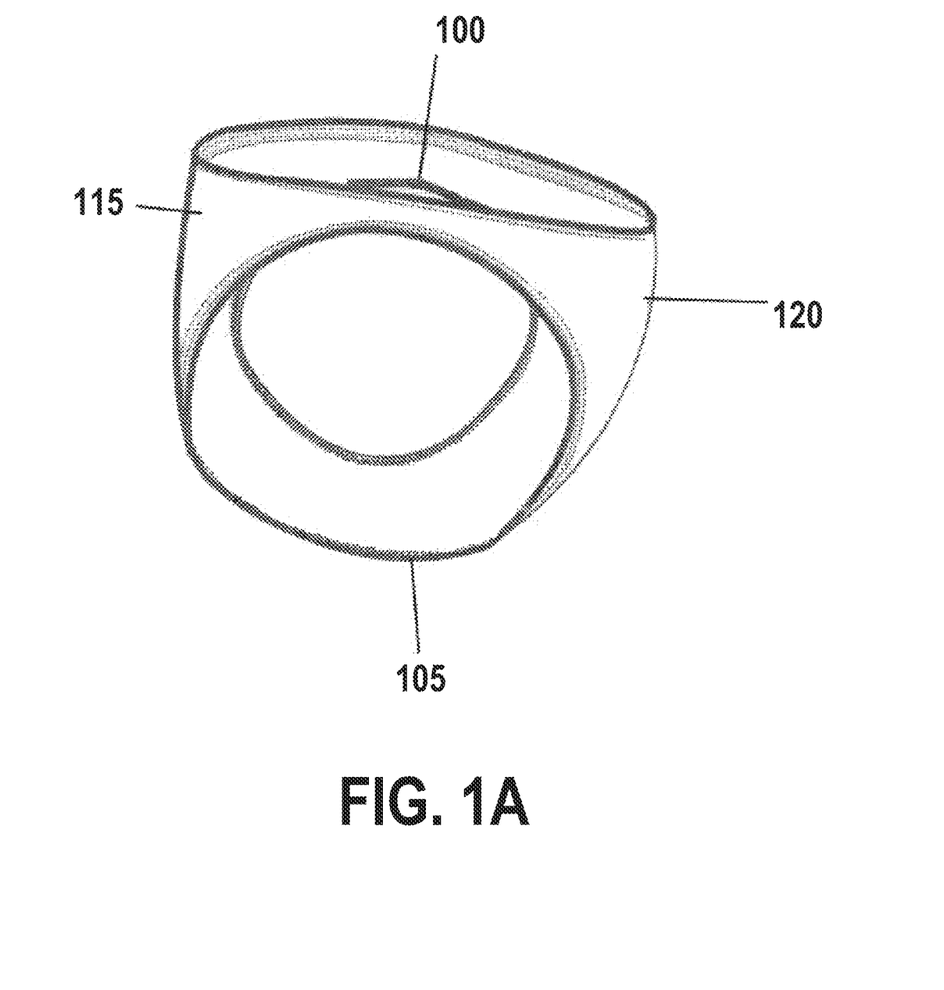
FIG. 1A is a left side view of the undergarment prior to attachment of a top crotch panel with center shaped hole.
Figure 1B:
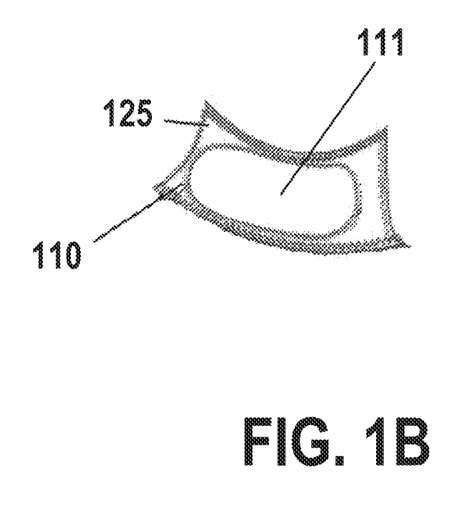
FIG. 1B is a left side view of a top crotch panel with center shaped hole.
Figure 1C:
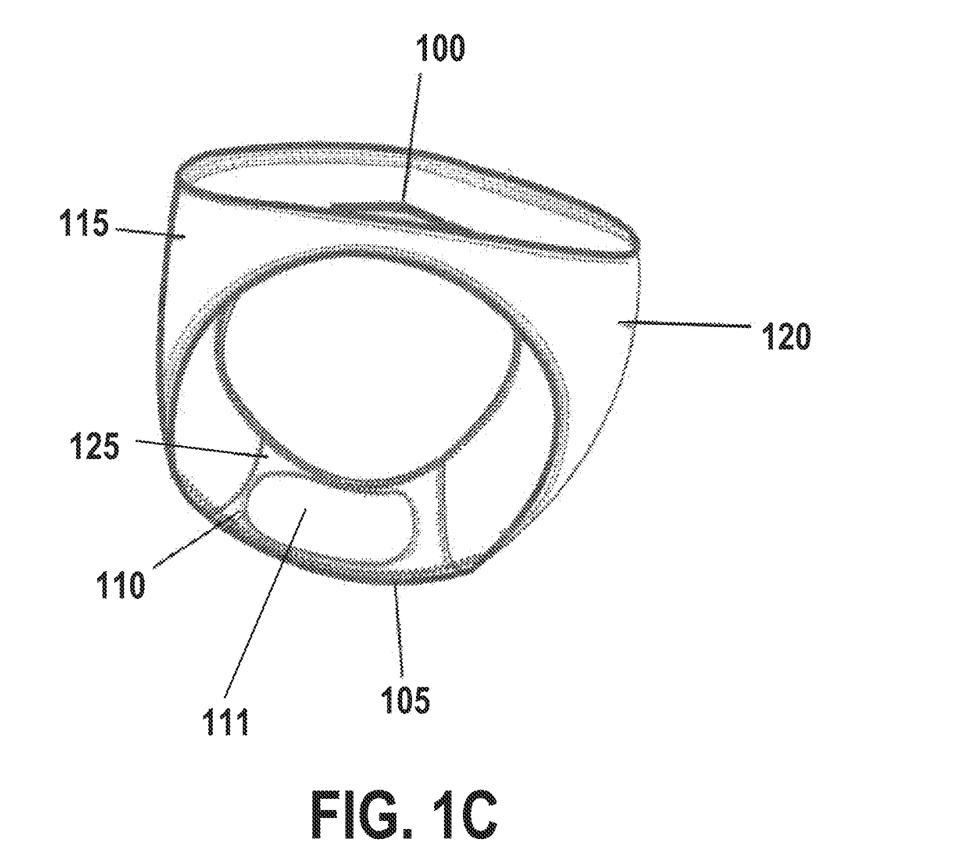
FIG. 1C is a left side view of the undergarment with the top crotch panel with center shaped hole attached thereto.
Figure 2:
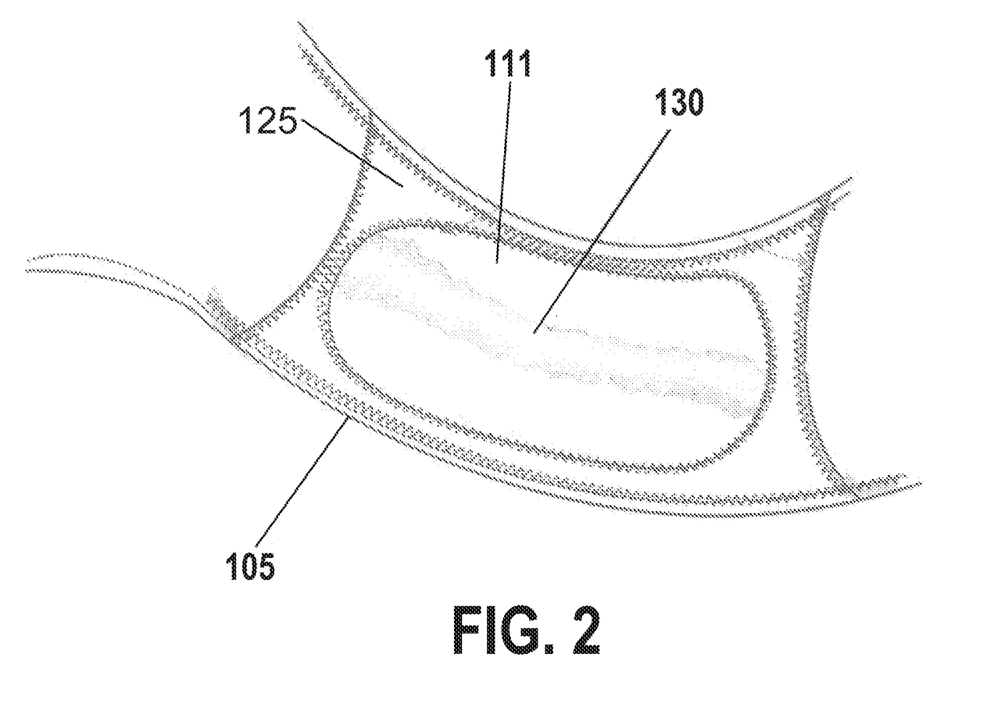
FIG. 2 is a top view of the crotch area.
Figure 3:
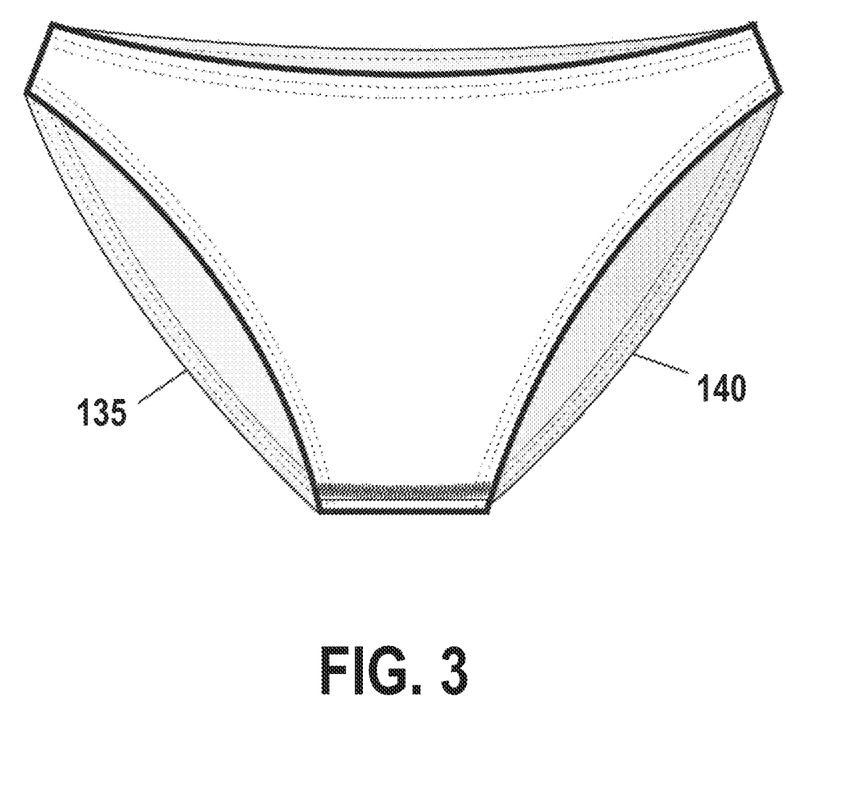
FIG. 3 is a front view of the undergarment leg opening.
Figure 4:
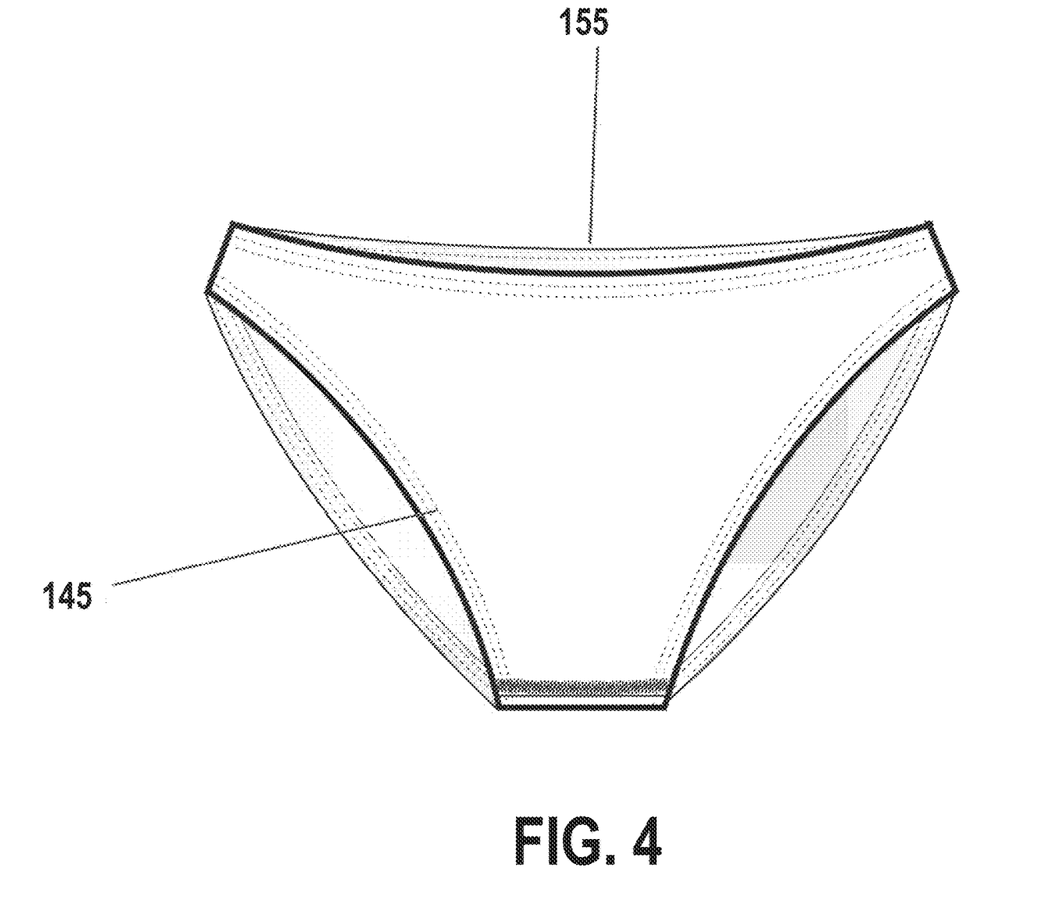
FIG. 4 is a front view of the undergarment.
Figure 5:
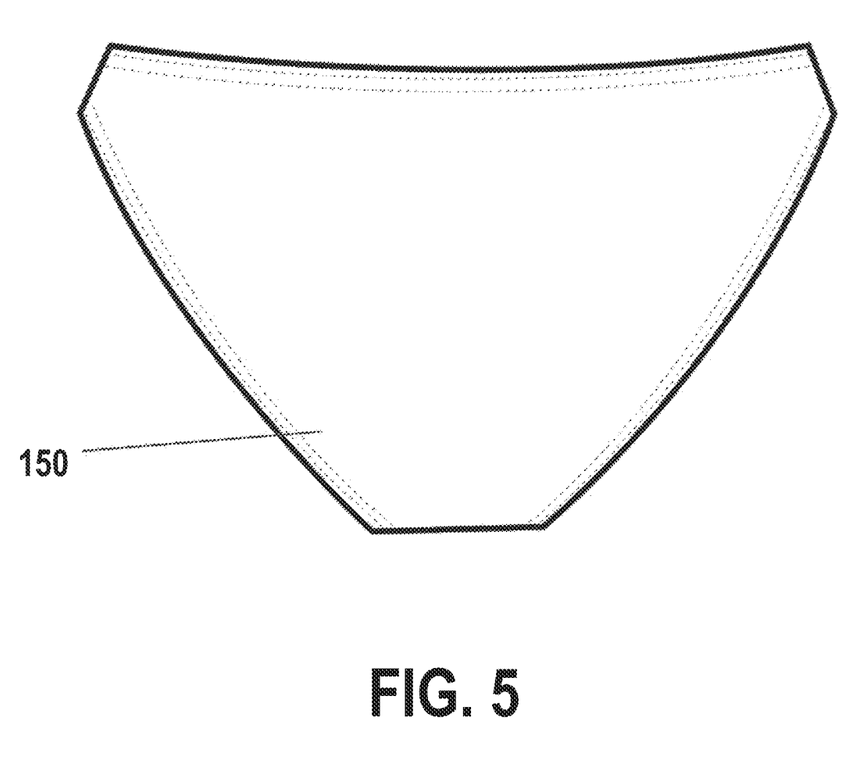
FIG. 5 is a back view of the undergarment.
Figure 6:
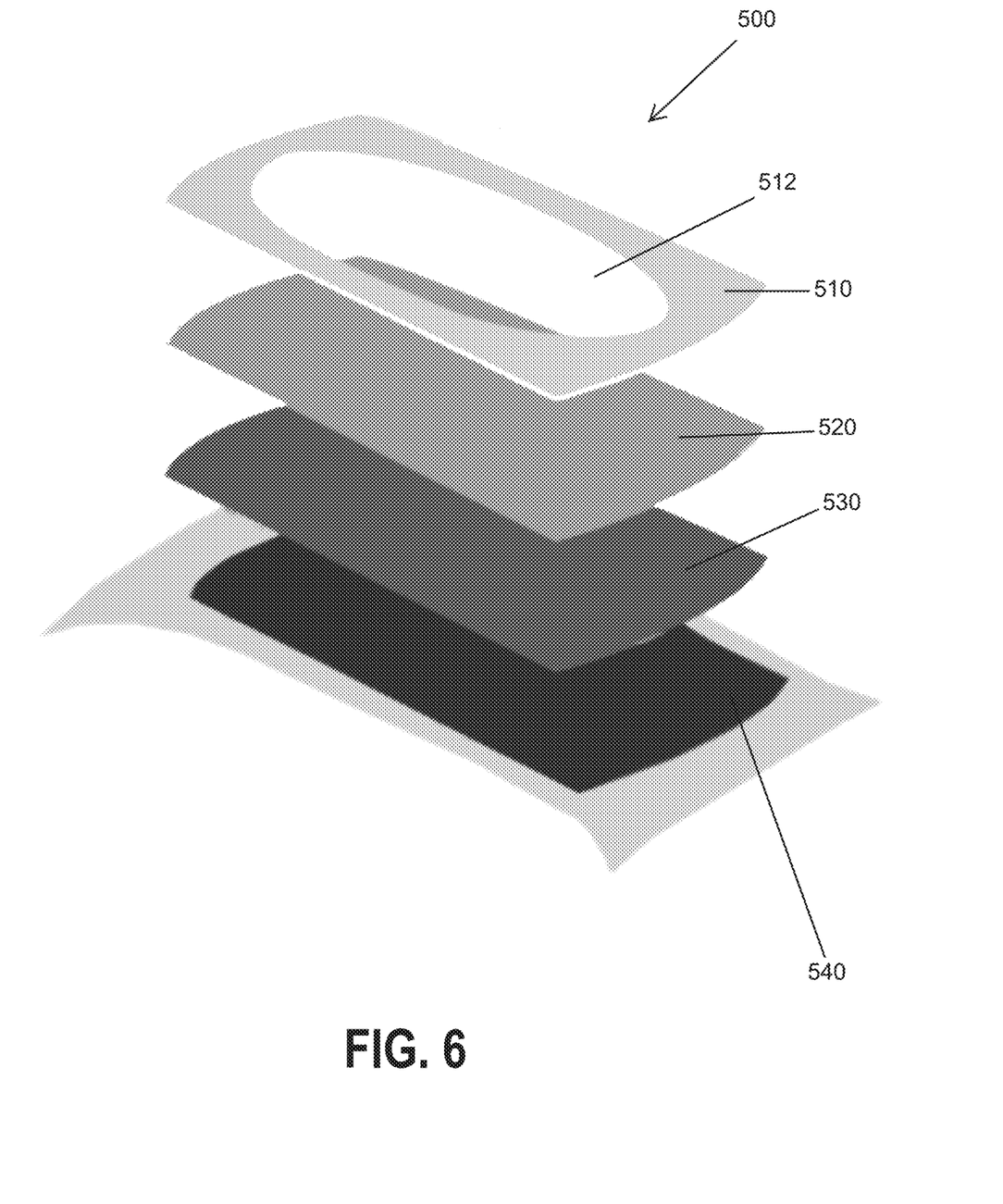
FIG. 6 is an exploded view of a crotch panel system.

As described above, in various instances the garment comprises more than two crotch area panels. The plurality of crotch area panels forms a crotch panel system. An exemplary crotch panel system 500 is shown in FIG. 6. The crotch panel system 500 comprises a top crotch area panel 510, wherein an aperture 512 is defined therein. In various instances, the aperture 512 is surrounded by an elastic border to facilitate insertion of an object, for example. In various instances, the top crotch area panel 510 is comprised of a dri-tech mesh material. The dri-tech mesh material is configured to collect and/or absorb fluid on contact. In other words, the dri-tech mesh material is configured to collect and/or fluid before it travels and/or spreads. The top crotch area panel 510 is configured to provide leak protection along all sides of the crotch panel system 500. The top crotch area panel 510 is further configured to assist in stopping front, side, and/or back leaks. The top crotch area panel 510 is configured to face inward toward the user when the garment is worn by the user. While the aperture 512 is configured to receive an object such as, for example, a sanitary pad, the crotch panel system 500 is configured to absorb fluid without the assistance of an additional object. The object is configured to be used as optional and/or additional leak protection.

A second crotch area panel 520 is positioned beneath the top crotch area panel 510. In various instances, the second crotch area panel 520 comprises organic cotton, cotton flannel, and/or any other suitable material. Among other things, the second crotch area panel 520 is configured to eliminate and/or reduce odor. The composition of the second crotch area panel 520 does not comprise plastic. In instances where an object is inserted through the aperture 512 of the top crotch area panel 510, the second crotch area panel 520 assists in holding the object in place. In other words, the second crotch area panel 520 and the top crotch area panel 510 cooperate to hold the object in place.

A third crotch area panel 530 is positioned beneath the second crotch area panel 520. In various instances, the third crotch area panel 530 comprises a wool-lined zorb material. The third crotch area panel 530 is a built-in absorbent liner. The third crotch area panel 530 is configured to absorb liquid. In various instances, the third crotch area panel 530 is configured to absorb the same amount of liquid as up to 2.5 regular and/or standard tampons. In various instances, third crotch area panel 530 is configured to absorb more than 2.5 regular and/or standard tampons.

A bottom crotch area panel 540 is positioned beneath the third crotch area panel 530. In various instances, the bottom crotch area panel 540 comprises a jersey mesh coated polytetrafluoroethene (PTFE) material. The bottom crotch area panel 540 is integrated with the other material, such as, for example, the front and/or back panels of the garment. The bottom crotch area panel 540 faces outward when the garment is worn by a user. The bottom crotch area panel 540 is angled in a manner that efficiently collects a flow of liquid. In various instances, the panels of the crotch panel system 500 cooperate to absorb liquid.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A crotch panel system, comprising:
   a bottom crotch panel;
   a unitary top layer crotch panel defining a shaped hole in the center, wherein the shaped hole defines a perimeter, wherein said unitary top layer crotch panel consists of a single piece of material;
   an elastic border extending around the perimeter of the shaped hole of the top layer crotch panel, wherein the elastic border is configured to stretch to facilitate insertion of an object; and
   an additional crotch panel layer attached to the bottom crotch panel to provide stability of the object placed within the crotch panel system, wherein the additional crotch panel layer is comprised of a fabric material.

2. The crotch panel system of claim 1, wherein the shaped hole is in the shape of an oval.

3. The crotch panel system of claim 1, wherein the shaped hole is in the shape of a square.

4. The crotch panel system of claim 1, wherein the object is concealed within the crotch panel system.

5. The crotch panel system of claim 1, wherein the additional crotch panel layer does not comprise plastic.

6. The crotch panel system of claim 1, wherein the additional crotch panel layer is configured to absorb liquid.

7. The crotch panel system of claim 1, wherein the crotch panel system is reusable.

8. The crotch panel system of claim 1, wherein the top crotch panel is configured to absorb liquid on contact.

9. A garment, comprising: a main body comprising a first crotch panel;
   a second crotch panel positioned above the first crotch panel, wherein the second crotch panel is comprised of fabric;
   a third crotch panel positioned above the second crotch panel, wherein a space is defined between the second crotch panel and the third crotch panel, wherein the space is configured to receive an object, and wherein the third crotch panel consists of a single piece of material, comprising:
   an outer perimeter, wherein the third crotch panel is attached to the main body along the outer perimeter; and
   an aperture centrally defined within the single piece of material, wherein the aperture comprises a perimeter, and wherein the perimeter is configured to stretch to facilitate placement of the object.

10. The garment of claim 9, wherein the garment is an undergarment.

11. The garment of claim 9, wherein the perimeter of the aperture comprises elastic.

12. The garment of claim 9, wherein the aperture comprises an elastic border.

13. The garment of claim 9, wherein the garment is comprised of at least one of cotton, lycra, nylon, lace, polyester, slinky, or spandex material.

14. The garment of claim 9, wherein the second crotch panel does not comprise plastic.

15. A garment, comprising: a main body; and a crotch panel system attached to the main body, wherein the crotch panel system comprises: a bottom crotch panel; a discrete middle crotch panel; and a top crotch panel, comprising: a perimeter, wherein the top crotch panel is attached to at least one of the middle crotch panel and the bottom crotch panel at the perimeter; wherein the top crotch panel consists of a single piece of material; and an aperture defined within the top crotch panel, wherein the top crotch panel is comprised of a dri-tech mesh material configured to absorb fluid on contact.

16. The garment of claim 15, wherein a pocket is defined between the middle crotch panel and the top crotch panel, wherein an object is configured to be concealed within the pocket, and wherein the object comprises an absorbent article.

17. The garment of claim 15, wherein the garment is an undergarment.

18. The garment of claim 15, wherein the crotch panel system is configured to absorb liquid.

19. The garment of claim 15, wherein the garment is comprised of at least one of cotton, lycra, nylon, lace, polyester, slinky, or spandex material.

20. The garment of claim 15, wherein the middle crotch panel is configured to absorb liquid.

* * * * *